(12) United States Patent
Fini et al.

(10) Patent No.: US 9,050,417 B2
(45) Date of Patent: Jun. 9, 2015

(54) MEMBRANE FOR A PRESSURE DOME

(75) Inventors: Massimo Fini, Mirandola (IT); Reinhold Reiter, Crema (IT); Luca Donarini, Azzano Mella (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 210 days.

(21) Appl. No.: 13/695,475

(22) PCT Filed: Apr. 20, 2011

(86) PCT No.: PCT/EP2011/056321
§ 371 (c)(1),
(2), (4) Date: Oct. 31, 2012

(87) PCT Pub. No.: WO2011/134859
PCT Pub. Date: Nov. 3, 2011

(65) Prior Publication Data
US 2013/0042692 A1 Feb. 21, 2013

(30) Foreign Application Priority Data
Apr. 30, 2010 (EP) ..................................... 10161554

(51) Int. Cl.
G01L 7/08 (2006.01)
A61M 1/36 (2006.01)
G01L 19/14 (2006.01)

(52) U.S. Cl.
CPC .............. *A61M 1/3639* (2013.01); *G01L 19/14* (2013.01); *A61M 1/3641* (2013.01)

(58) Field of Classification Search
None
See application file for complete search history.

(56) References Cited

U.S. PATENT DOCUMENTS

| 4,462,409 | A | * | 7/1984 | Pace et al. ..................... 600/488 |
| 4,781,686 | A |   | 11/1988 | Erickson |
| 5,563,347 | A | * | 10/1996 | Martin et al. ................... 73/756 |
| 6,725,726 | B1 | * | 4/2004 | Adolfs et al. ................... 73/756 |
| 7,603,907 | B2 |   | 10/2009 | Reiter et al. |
| 2003/0115965 | A1 |   | 6/2003 | Mittelstein et al. |
| 2004/0050168 | A1 | * | 3/2004 | Uberreiter ....................... 73/706 |
| 2004/0168530 | A1 | * | 9/2004 | Adolfs et al. ................ 73/866.5 |
| 2007/0295093 | A1 |   | 12/2007 | Reiter et al. |

FOREIGN PATENT DOCUMENTS

| CN | 101035577 |   | 9/2007 |
| DE | 3421149 | A1 * | 12/1984 |
| WO | WO 02/03854 |   | 1/2002 |
| WO | WO 2006/053673 |   | 5/2006 |
| WO | WO 2007/056363 |   | 5/2007 |

* cited by examiner

*Primary Examiner* — Andre Allen
(74) *Attorney, Agent, or Firm* — Jacobson Holman, PLLC.

(57) ABSTRACT

A membrane for a pressure dome is configured to cooperate with a pressure sensor, and includes a resilient circular wall and a circular rim. The resilient circular wall is configured to close one side of the pressure dome so as to define a partition between the inside of the pressure dome and the outside. The circular rim is configured to be housed in a main body of the pressure dome. The membrane is configured such that the resilient circular wall, when there is no difference between the pressures acting respectively on the inner surface and on the outer surface, has an outwardly convex form.

15 Claims, 6 Drawing Sheets

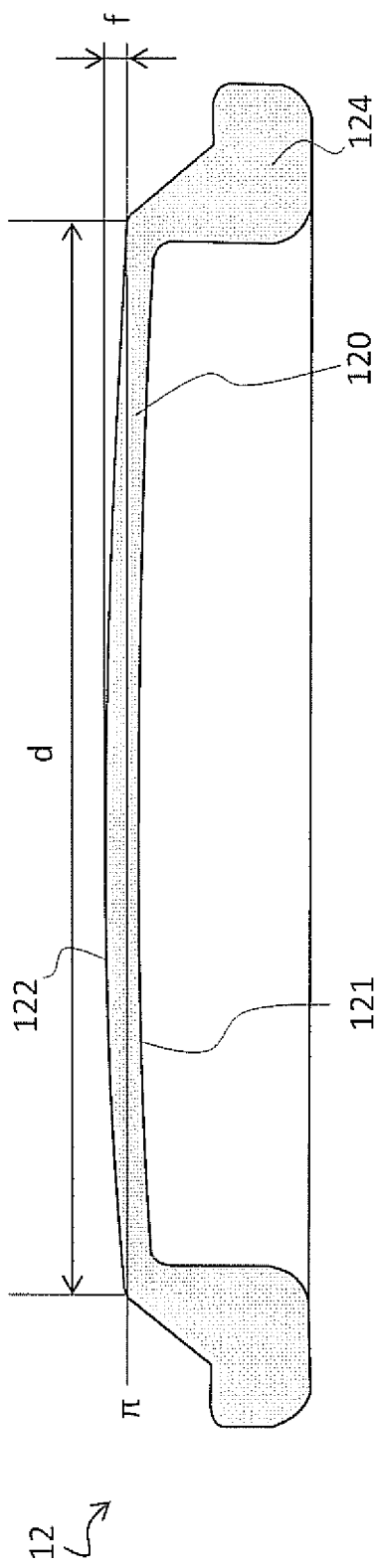
Fig. 3.a
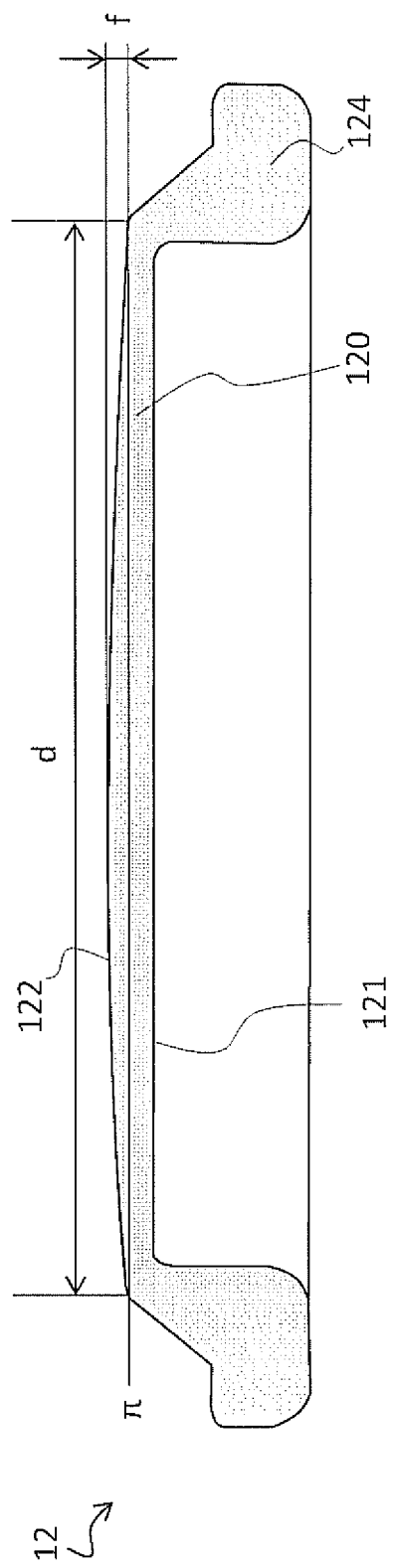
Fig. 3.b

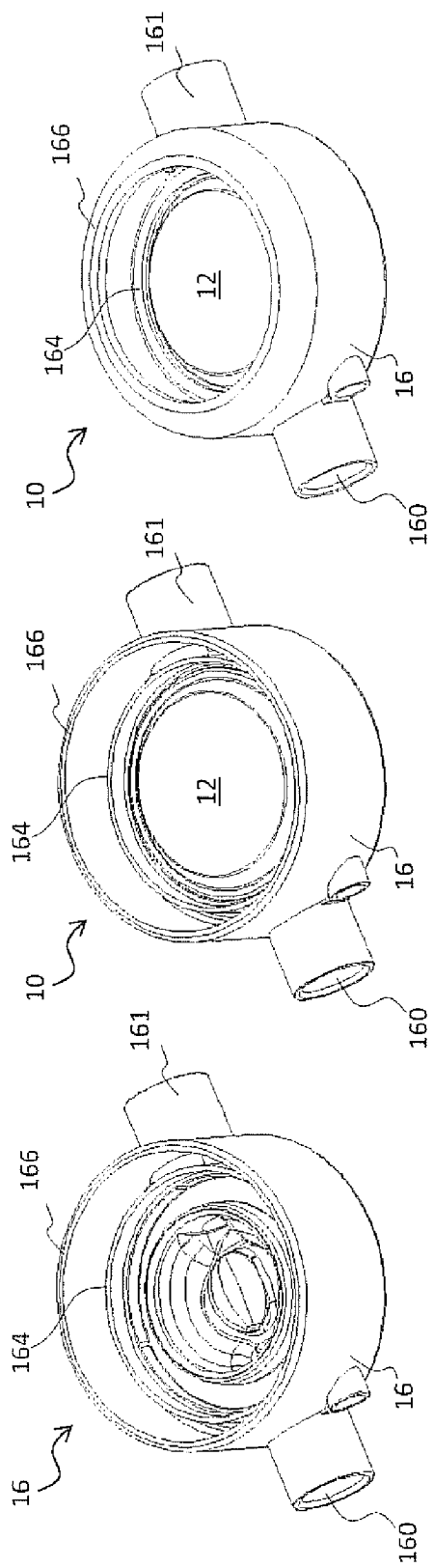
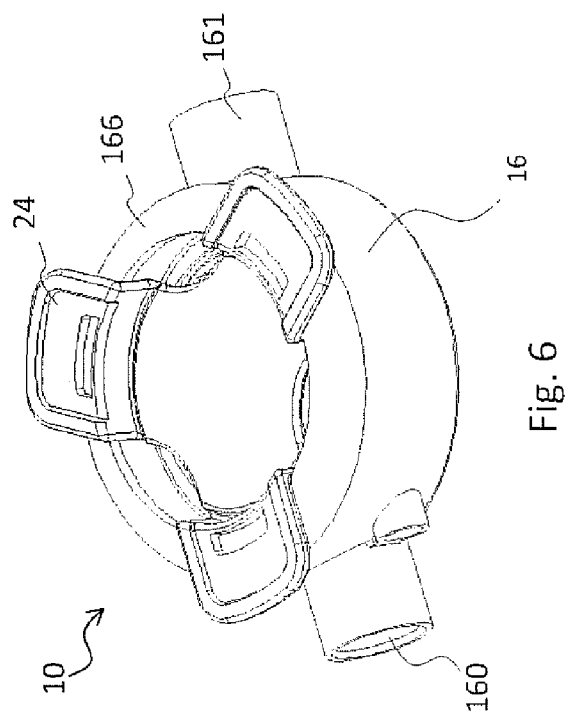

MEMBRANE FOR A PRESSURE DOME

CROSS-REFERENCE TO RELATED APPLICATIONS

This is a national stage of PCT/EP11/056321 filed Apr. 20, 2011 and published in English, which has a priority of Europe no. 10161554.0 filed Apr. 30, 2010, hereby incorporated by reference.

BACKGROUND OF THE INVENTION

1. Field of Invention

The present invention relates to a chamber for measuring the pressure inside a pipe, in particular in an extra-corporeal circuit.

2. Description of Prior Art

During therapeutic treatment requiring extra-corporeal circulation, as for example in the case of hemodialysis, the pressure inside the circuit must be monitored. For this purpose, the machine used for the therapeutic treatment usually comprises suitably designed sensors. It is obviously necessary to prevent the fluids contained in the circuit from contaminating these sensors which are intended to be used repeatedly. On the other hand, the extra-corporeal circulation is performed in a disposable circuit.

For this purpose it is known to provide the circuit with at least one pressure chamber, usually called a "pressure dome", suitable for creating an interface between the circuit and the pressure sensor. The pressure dome usually comprises a housing with an inlet and outlet which are respectively connected to the circuit. Finally an elastomer membrane closes one side of the chamber and is formed so as to be able to make contact with a pressure sensor. The elastomer membrane is highly resilient so that it is able to transmit to the sensor the pressure present inside the circuit and the associated variations. A pressure dome of this type is schematically shown in FIG. 1 and is described in detail in the U.S. Pat. No. 7,603,907.

These pressure domes, although widely used, are however not defect-free.

A first defect consists in the fact that air may infiltrate between the membrane and the sensor. This phenomenon may occur, for example, when the sensor is joined to the pressure dome. During positioning of the sensor it is possible in fact for an air pocket to remain trapped between the two surfaces which instead should remain in direct contact. In such a case the sensor is no longer able to measure adequately the pressure of the chamber nor provide a reliable response with regard to variations thereof.

This problem is further exacerbated should the circuit have internally a negative pressure, i.e. a pressure lower than atmospheric pressure. In such a case, which typically occurs upstream of the pumps located along the circuit, the membrane assumes a concave form, i.e. is "sucked" towards the inside of the pressure dome and worsen the precision of measurement.

Furthermore there exists the problem of ageing of the elastomer from which the membrane is made. This ageing results in the loss of flatness of the membrane. It is clear that a membrane which has lost its elasticity and its flatness may easily result in the formation of air pockets between the pressure sensor and the membrane itself. It should be remembered in this connection that the pressure domes and associated membranes are generally intended to have a shelf life of several years from time of production to actual use. This shelf life, which is quite reasonable from a logistical point of view, risks a loss of its design characteristics.

Another problem of the pressure dome of the known type is instead associated with the technology which is currently used to manufacture it. The main body of the chamber is made, in a manner known per se, by means of molding of a polymer which is sufficiently rigid and suitable for contact with the physiological fluids. The elastomer membrane, instead, is made by means of two-component injection molding which is used to produce, in addition to the actual elastomer membrane, also a fixing ring made with a rigid polymer, for example such as that used for the main body. The elastomer membrane and the associated ring thus form a single part made of two different materials. They are then joined to the main body, for example by means of a screw/female-thread, snap-engaging, interference or similar connection.

The manufacture of the pressure dome of the known type, which comprises a two-component injection molding operation, therefore requires the use of molds with movable parts, the manufacture and use of which are somewhat complex. Moreover these movable-part moulds require an initial outlay which is distinctly greater than that of ordinary molds.

SUMMARY OF THE INVENTION

The object of the present invention is therefore to overcome at least partly the drawbacks mentioned above with reference to the prior art.

In particular, one task of the present invention is to provide a membrane for a pressure dome which is able to reduce to a minimum the possibility of air entering into the joint with the pressure sensor.

Another task of the present invention is to provide a pressure dome which may be made with simple and reliable technology, while still ensuring the high level of quality associated with the pressure domes of the known type.

The abovementioned object and tasks are achieved by a membrane and by a pressure dome as described herein.

BRIEF DESCRIPTION OF DRAWINGS

The characteristic features and further advantages of the invention will become clear from the description, provided hereinbelow, of a number of examples of embodiment provided purely by way of a non-limiting example with reference to the accompanying drawings.

FIG. 3.a shows schematically a cross-sectioned side view of a membrane according to the invention;

FIG. 3.b shows schematically a cross-sectioned side view of another membrane according to the invention;

FIG. 5a-5c shows schematically three successive stages during assembly of a pressure dome according to the invention;

FIG. 6 shows a pressure dome according to the invention combined with a multi-use protective element;

DETAILED DESCRIPTION OF THE PREFERRED EMBODIMENTS

Figure 1:
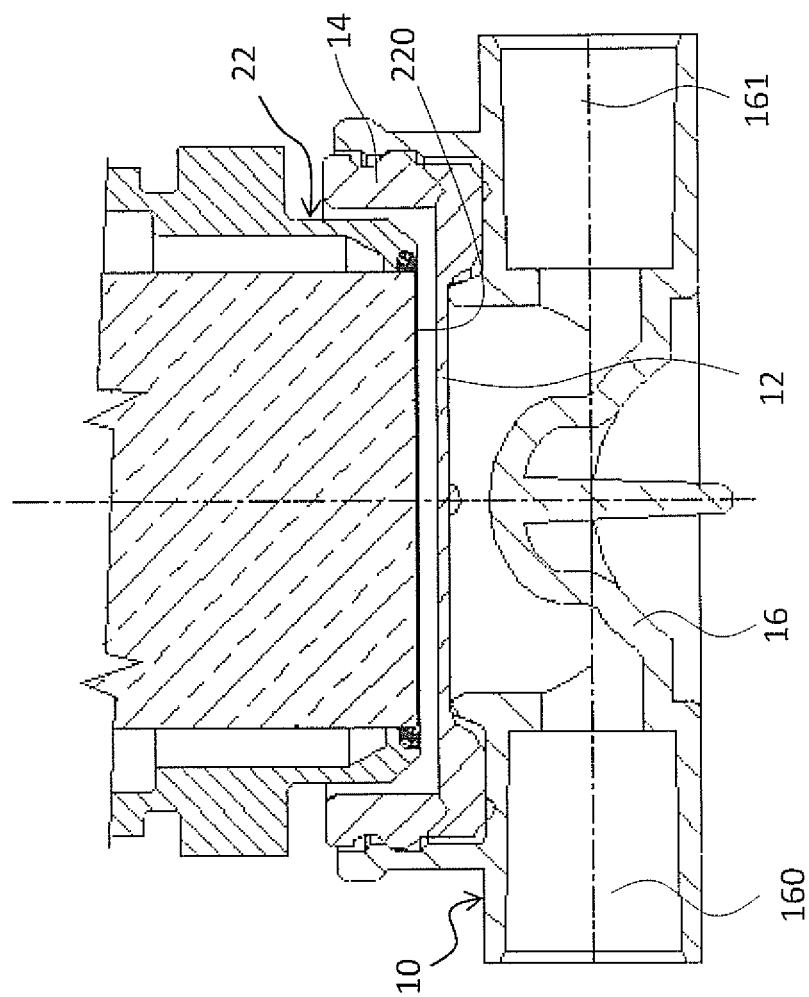
FIG. 1 shows schematically a cross-sectioned side view of a pressure dome according to the prior art.

Further scope of applicability of the present invention will become apparent from the detailed description given herein-after. However, it should be understood that the detailed description and specific examples, while indicating preferred embodiments of the invention, are given by way of illustration only, since various changes and modifications within the spirit and scope of the invention will become apparent to those skilled in the art from this detailed description.

With reference to the accompanying figures, 10 denotes in its entirety a pressure dome comprising a membrane 12.

The membrane 12 according to the invention comprises:
- a resilient circular wall 120 suitable for closing one side of the pressure dome 10 so as to define a partition between the inside of the pressure dome and the outside;
- a circular rim 124 suitable for being joined to a main body 16 of the pressure dome 10;

whereby the resilient circular wall 120, when there is no difference between the pressures acting respectively on the inner surface 121 and on the outer surface 122, has an outwardly convex form.

Hereinbelow "inner" is understood here as meaning the part of the pressure dome 10 which, during use, is occupied by the physiological liquid. In relation to the membrane 12, therefore, the inner surface 121 is that surface which, during use, is wetted by the physiological liquid.

The membrane 12 therefore is not flat, but is characterized by a double curvature. In other words, the resilient circular wall 120 assumes the form of a cap, for example a cap forming part of a sphere or other solid of rotation. In accordance with such a geometrical form, a maximum elevation f may be specifically defined for the resilient circular wall 120. In this connection, see the diagrams in FIG. 3. This maximum elevation f is the distance between the outermost point of the cap and the plane $\pi$ containing the outer base circumference of the cap itself.

In accordance with certain embodiments of the invention, the cap defined by the resilient circular wall 120 has a maximum elevation of between 1% in 2% of the diameter d of the base circumference of the cap.

In accordance with the embodiment of the invention shown in FIG. 3, the cap defined by the resilient circular wall 120 has a maximum elevation f equal to about 1.7% of the diameter d of the base circumference of the cap. In particular, in this embodiment, the diameter d is equal to 17.7 mm and the maximum elevation f is equal to 0.3 mm.

As already described above, the resilient circular wall 120 has an outwardly convex form, provided that there is no difference between the pressures acting on the inner surface 121 and on the outer surface 122 respectively. According to the embodiment of FIG. 3.*a*, both the inner surface 121 and the outer surface 122 have outwardly convex form. In such embodiment, the circular wall 120 has an almost uniform thickness. According to the embodiment of FIG. 3.*b*, while the outer surface 122 has an outwardly convex form, the inner surface 121 is substantially flat. In such embodiment, the thickness of the circular wall 120 slightly varies along the radial direction, i.e. has a maximum in the centre of the wall 120 (i.e. the outermost point) and gradually reduces toward its periphery.

The membrane 12, as shown in FIG. 3, is preferably made as one piece. In other words, the rim 124 is preferably formed integrally and as one piece with the wall 120. Even more preferably, the rim 124 and wall 120 are made by means of injection-molding of a single material. For example, the membrane 12 according to the invention may be made, in a manner known per se, using a thermoplastic elastomer or other elastomers suitable for contact with the physiological fluids.

The circular rim 124 has a cross-section which is distinctly thicker than that of the wall 120. With particular reference to FIG. 3, it can be noted how the thickness of the circular rim 124 (measured in a direction substantially perpendicular to the plane $\pi$) is about three times that of the wall 120 (measured in the same way). This results, for the same material used, in a greater rigidity of the rim 124 compared to the rest of the membrane 12, in particular compared to the wall 120.

The relative rigidity of the rim 124 is necessary in order to be able to fix effectively and stably the membrane 12 to the main body 16 of the pressure dome 10. The joint between the membrane 12 and the main body 16 is described in more detail below.

As can be clearly seen in FIG. 1, the resilient circular wall 120 of the membrane 12 according to the prior art is perfectly flat. In this way, the end surface 220 of the pressure sensor 22, which is also flat, may ideally rest on the resilient circular wall 120, without trapping any air pockets. It should be noted, however, that, as already discussed in the introduction, in reality it is unlikely for the ideal operating conditions to be present. This means that, in reality, the membrane often is not flat as it should be and that therefore the air may easily remain trapped between the pressure sensor 22 and the membrane 12.

The outwardly convex form of the membrane 12 according to the invention eliminates this risk. In fact, the contact between the membrane 12 and the end surface 220 takes place gradually, starting from the centre (i.e. the outermost point of the wall 120) and gradually extending towards the periphery. In this way, the air is expelled progressively towards the outside. Moreover, the convex form of the membrane 12 has the effect that, even following relaxation due to ageing of the elastomer or the operating conditions affecting the membrane 12, the wall 120 is able to still perform its function. Such relaxation will result in the worst of cases in a reduction in the maximum elevation f, but is unlikely to eliminate it entirely and/or reverse the curvature of the wall 120 so that it becomes concave.

The function of the membrane 12, as mentioned above also with reference to the prior art, is to transmit to the sensor 22 the pressure of the fluid and associated variations. From this point of view, the membrane is therefore able to perform its function more effectively, the less it alters the progression of the pressure and the more accurately it transmits it. For this reason, the ideal membrane has always been considered to be that which, having a perfectly flat extension, is not able to generate reaction forces outside of its plane. The membrane according to the invention instead, being convex, appears to differ markedly from this ideal model. The Applicant has instead noted how, surprisingly, the convex membrane according to the invention also transfers accurately the pressure progression. Specific tests carried out in this connection by the Applicant have shown how the behavior of the convex membrane according to the invention is, from the point of view of the transmission of the pressure, absolutely comparable to that of a flat membrane of the known type. On the other hand, however, the convex membrane according to the invention introduces substantial improvements from the point of view of expulsion of the air and reaction to ageing of the elastomer.

The invention also relates to a pressure dome 10 for cooperating with a pressure sensor 22, comprising a membrane 12 according to the invention. The pressure dome 10 according to the invention comprises, in a manner known per se, a main body 16. The main body 16 defines an inlet 160 and an outlet 161 allowing hydraulic connection to a pipe, for example the pipe of an extra-corporeal circuit.

In accordance with certain embodiments, the main body 16 also defines a seat 162 for stably seating the membrane 12; the seat 162 is in particular formed so as to receive the rim 124 of the membrane 12.

The main body 16 is preferably produced, in a manner known per se, by means of injection-molding of a polymer which is sufficiently rigid and suitable for contact with the physiological fluids. Polymers suitable for this type of use may be, for example: polycarbonate (PC), polypropylene (PP), polyethylene (PE), polystyrene (PS), polyvinyl chloride (PVC), polyethylene terephthalate (PET), polybutylene terephthalate (PBT), acrylonitrile-butadiene-styrene (ABS), and copolyesters.

Figure 2:
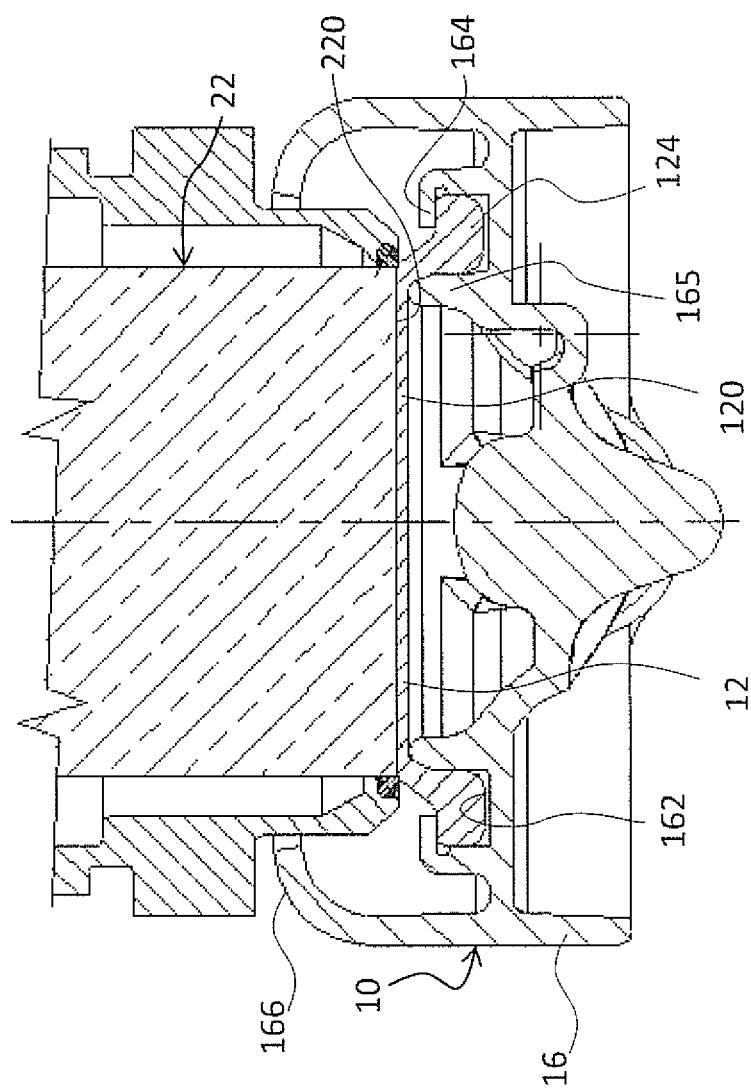
FIG. 2 shows schematically a cross-sectioned side view of a pressure dome according to the invention.
Figure 4:
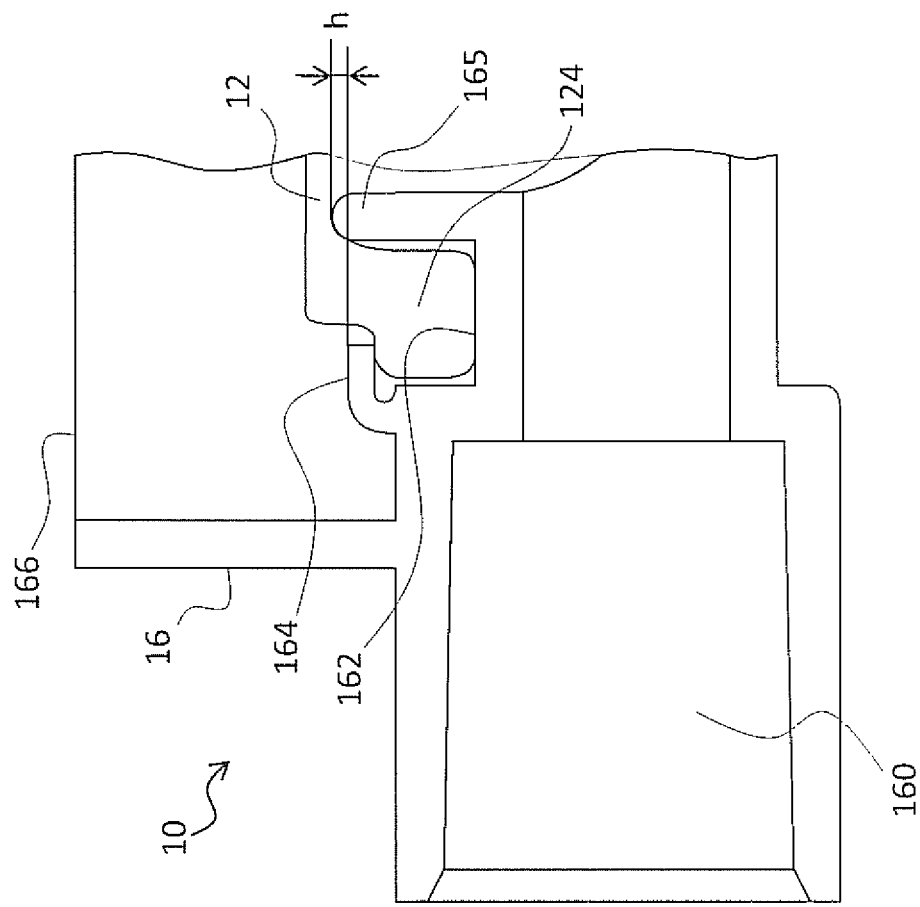
FIG. 4 shows schematically a detail of a cross-sectioned side view of the joint between the membrane and the pressure dome according to invention.

In accordance with the embodiments shown in FIGS. 2 and 4, the seat 162 is defined by an edge 164 and by an inner wall 165. The edge 164 allows the membrane 12 to be fixed inside the seat 162. In accordance with these embodiments, the main body 16 is preferably produced with the edge 164 formed as a cylindrical wall (see specifically FIG. 5.a). At the time of assembly of the main body 16 and the membrane 12, in order to form the complete pressure dome 10, the rim 124 of the membrane 12 is housed inside the corresponding seat 162 (see specifically FIG. 5.b). Then the edge 164 is folded over so as to press against the rim 124 of the membrane 12 and thus keep it inside the corresponding seat 162 (see specifically FIG. 5.c and FIG. 4).

This system for fixing the membrane 12, achieved by means of deformation of the edge 164, is referred to as beading. Deformation of the edge 164 may be achieved, in a manner known per se in relation to the processing of polymers, by means of the application of heat, ultrasound or rotary friction. Beading is performed so that the pressure dome is sealed in its entirety, except obviously for the openings which form the inlet 160 and the outlet 161. In other words, the joint between the membrane 12 and the main body 16 must prevent the physiological liquid, intended to occupy the pressure dome 10, from entering between the seat 162 and the membrane 12 and therefore escaping outwards.

In accordance with certain embodiments, for example that shown in FIG. 4, after the beading operation, the edge 164 is lower than the inner wall 165 which defines, together with the said edge 164, the seat 162. With reference to FIG. 4, the difference in height between the edge 164 after the beading operation and the inner wall 165 is indicated by h. In accordance with certain embodiments, the height h may range between 0.01 and 0.3 mm. In accordance with the embodiment shown in FIG. 4, the difference h is equal to about 0.15 mm.

The difference in height h between the inner wall 165 and the edge 164 ensures a more functional contact between the end wall 220 of the pressure sensor 22 and the membrane 12 of the pressure dome 10. When contact occurs between the end wall 220 and the membrane 12, it is the reaction of the wall 165 which defines the contour of the area intended to transmit the pressure from the pressure dome 10 to the sensor 22. The contour defined by the inner wall 165 includes only the active surface for transmission of the pressure. This structure therefore ensures that the pressure is transmitted in an optimum manner.

In accordance with certain embodiments, the main body 16 comprises a second outer edge 166. In FIG. 4 this edge is formed as a cylindrical wall, while in FIG. 2 it is shown folded inwards in a manner similar to that explained above in connection with the edge 164. Unlike the edge 164, the second edge 166 is not intended to cooperate with other components of the pressure dome 10. The beading of the second edge 166 may, however, be advantageous during cooperation of the pressure dome 10 with the pressure sensor 22. The second edge 166, when folded over as shown in FIG. 2, may in fact assist centering of the sensor 22 on the membrane 12 when they are joined together.

FIG. 6 shows a pressure dome 10 according to the invention combined with a multi-use protective element 24. This element is designed to protect the membrane 12 during all the stages of the life of the pressure dome 10, from the time of assembly until its final use in an extra-corporeal circuit. The multi-use protective element 24 is designed to be combined with the pressure dome 10, in particular in the position intended to receive the pressure sensor 22. In this way, the multi-use protective element 24 is able to prevent damage to the membrane resulting from accidental knocks or contact which may occur during the logistical operations such as handling, packaging, transportation, storage, etc.

The need to protect the membrane arises from the fact that the pressure dome according to the invention must be assembled in its final form in a production plant and therefore far from the location of its final use. Assembly, in fact, owing to the beading operation, requires the use of specific machinery. On the other hand, assembly of the pressure dome according to the prior art may be performed manually, even at the time of final use, by joining a main body 16 together with a respective membrane 12. The membrane 12 according to the prior art may therefore be carefully stored separately until the time of its final use, thus avoiding any damage. The protective element 24 is defined as being multi-use because, since it is not intended to come into contact with the physiological fluids, it may be re-used several times.

Figure 7:
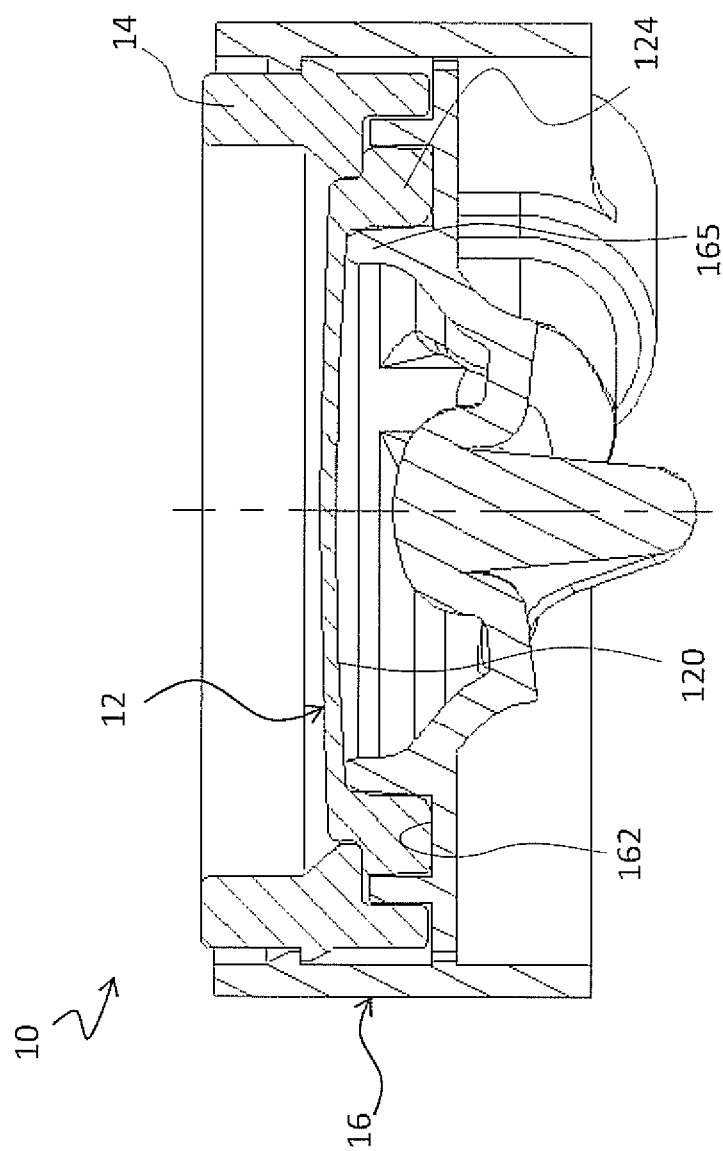
FIG. 7 shows schematically a cross-sectioned side view of another pressure dome according to the invention.

According to other embodiments, for example that shown in FIG. 7, the membrane 12 is convex, as described above in connection with the present invention, but is fixed to the main body 16 by means of a rigid ring 14, as described in relation to the prior art.

According to these embodiments, the membrane 12 is able to achieve all the advantages described above with regard to the convex form. Fixing of the membrane 12 onto the main body 16 of the pressure dome 10, however, is not achieved by means of beading, but by means of a rigid ring 14 suitable for defining a joint with the main body 16. FIG. 7 shows a snap-engaging connection between the ring 14 and the main body 16, but it may also be a screw/female-thread, interference, or similar connection.

With these embodiments it is possible to combine the advantages of the convex membrane with the advantage of being able to assemble the pressure dome at the time of final use. In other words, in the embodiment according to FIG. 7, the membrane 12 may be carefully stored separately and there is therefore no need to preassemble the protective element 24.

According to certain embodiments, the membrane 12 and the ring 14 are manufactured separately, each one being able to be made for example by means of molding of a suitable material. Typically the ring 14 may be made using one of the polymers listed above with reference to the main body 16. The membrane 12, instead, may be advantageously made using a thermoplastic elastomer or other elastomers suitable for contact with the physiological fluids.

According to other embodiments, the membrane 12 and the ring 14 are instead made by means of two-component injection molding. A single part made with two different materials is thus obtained, as already described in connection with the prior art.

In the light of the above description it will be clear to the person skilled in the art how the membrane 12 and the pressure dome 10 according to the invention are able to overcome, at least partly, the disadvantages mentioned in connection with the prior art. In particular, the convex membrane 12 according to the invention is able to reduce to a minimum the possibility of air entering into the joint with the pressure sensor 22.

Moreover, the pressure dome 10 according to the invention, in the embodiments which do not require two-component injection molding, may be made using simple and reliable technology, while still ensuring the high level of quality associated with the pressure domes of the known type.

In connection with the embodiments of the membrane and the pressure dome described above, the person skilled in the art, in order to satisfy specific requirements, may make modifications to and/or replace elements described with equivalent elements, without thereby departing from the scope of the accompanying claims.

What is claimed is:

1. A membrane for a pressure dome, said membrane comprising:
    a resilient circular wall configured to close one side of said pressure dome so as to define a partition between an inside of the pressure dome and an outside of the pressure dome; and
    a circular rim configured to be housed in a main body of the pressure dome, the resilient circular wall, when there is no difference between pressures acting respectively on an inner surface thereof and on an outer surface thereof, having an outwardly convex form.

2. The membrane according to claim 1, wherein the resilient circular wall, when there is no difference in the pressures acting respectively on the inner surface and on the outer surface, has a form of a cap.

3. The membrane according to claim 2, wherein the resilient circular wall has a maximum elevation f, equal to a distance between an outermost point of the cap and a plane $\pi$ containing an outer base circumference of the cap, said maximum elevation f being between 1% and 2% of a diameter d of a base circumference of the cap.

4. The membrane according to claim 1, wherein the membrane is configured as one piece, with the rim being configured integrally and as one piece with the wall.

5. The membrane according to claim 1, wherein the membrane has a material of construction that is a thermoplastic elastomer.

6. The membrane according to claim 1, further comprising a rigid ring configured to define a joint with the main body of the pressure dome.

7. A pressure dome for cooperating with a pressure sensor, said pressure dome comprising:
    a main body which defines an inlet and an outlet configured to enable hydraulic connection to a pipe, and
    a membrane according to claim 1.

8. The pressure some according to claim 7, wherein the main body includes a seat for stably seating the membrane.

9. The pressure dome according claim 7, wherein the main body is configured as an injection molded polymer which is sufficiently rigid and configured for contact with physiological fluids, said polymer being selected from the group consisting polycarbonate (PC), polypropylene (PP), polyethylene (PE), polystyrene (PS), polyvinyl chloride (PVC), polyethylene terephthalate (PET), polybutylene terephthalate (PBT), acrylonitrile-butadiene-styrene (ABS), and copolyesters.

10. The pressure dome according to claim 8, wherein the seat includes an edge and an inner wall, and wherein the edge enables fixing of the membrane inside the seat by a beading.

11. The pressure dome according to claim 10, wherein the beading seals an entirety of the pressure dome.

12. The pressure dome according to claim 10, wherein the edge after the beading is lower than the inner wall.

13. The pressure dome according to claim 7, wherein the main body includes a second outer edge folded towards an inside thereof by a beading.

14. The pressure dome according to claim 7, further comprising a protective element configured to (i) be combined with the pressure dome in a position intended to receive the pressure sensor and (ii) protect the membrane.

15. The pressure dome according to claim 7, further comprising a rigid ring that fixes the membrane onto the main body of the pressure dome.

* * * * *

UNITED STATES PATENT AND TRADEMARK OFFICE
CERTIFICATE OF CORRECTION

PATENT NO.       : 9,050,417 B2
APPLICATION NO.  : 13/695475
DATED            : June 9, 2015
INVENTOR(S)      : Massimo Fini et al.

It is certified that error appears in the above-identified patent and that said Letters Patent is hereby corrected as shown below:

In the Claims

In column 8, claim 8, line 12, please change the word "some" to --dome--.

In column 8, claim 9, line 18, please add the word --of-- between the words "consisting" and "polycarbonate (PC).".

Signed and Sealed this
Sixteenth Day of August, 2016

Michelle K. Lee
*Director of the United States Patent and Trademark Office*

EX PARTE REEXAMINATION CERTIFICATE (11795th)

United States Patent
Fini et al.

(10) Number: US 9,050,417 C1
(45) Certificate Issued: Jan. 15, 2021

(54) MEMBRANE FOR A PRESSURE DOME

(75) Inventors: Massimo Fini, Mirandola (IT); Reinhold Reiter, Crema (IT); Luca Donarini, Azzano Mella (IT)

(73) Assignee: FRESENIUS MEDICAL CARE DEUTSCHLAND GMBH, Bad Homburg (DE)

Reexamination Request:
No. 90/014,411, Nov. 15, 2019

Reexamination Certificate for:
Patent No.: 9,050,417
Issued: Jun. 9, 2015
Appl. No.: 13/695,475
PCT Filed: Apr. 20, 2011
PCT No.: PCT/EP2011/056321
§ 371 (c)(1),
(2), (4) Date: Oct. 31, 2012
PCT Pub. No.: WO2011/134859
PCT Pub. Date: Nov. 3, 2011

Certificate of Correction issued Aug. 16, 2016

(30) Foreign Application Priority Data

Apr. 30, 2010 (EP) .................................... 10161554

(51) Int. Cl.
*G01L 7/08* (2006.01)
*A61M 1/36* (2006.01)
*G01L 19/14* (2006.01)

(52) U.S. Cl.
CPC ........... *G01L 19/14* (2013.01); *A61M 1/3639* (2013.01); *A61M 1/3641* (2014.02); *G01L 7/08* (2013.01)

(58) Field of Classification Search
None
See application file for complete search history.

(56) References Cited

To view the complete listing of prior art documents cited during the proceeding for Reexamination Control Number 90/014,411, please refer to the USPTO's public Patent Application Information Retrieval (PAIR) system under the Display References tab.

*Primary Examiner* — Catherine S Williams

(57) ABSTRACT

A membrane for a pressure dome is configured to cooperate with a pressure sensor, and includes a resilient circular wall and a circular rim. The resilient circular wall is configured to close one side of the pressure dome so as to define a partition between the inside of the pressure dome and the outside. The circular rim is configured to be housed in a main body of the pressure dome. The membrane is configured such that the resilient circular wall, when there is no difference between the pressures acting respectively on the inner surface and on the outer surface, has an outwardly convex form.

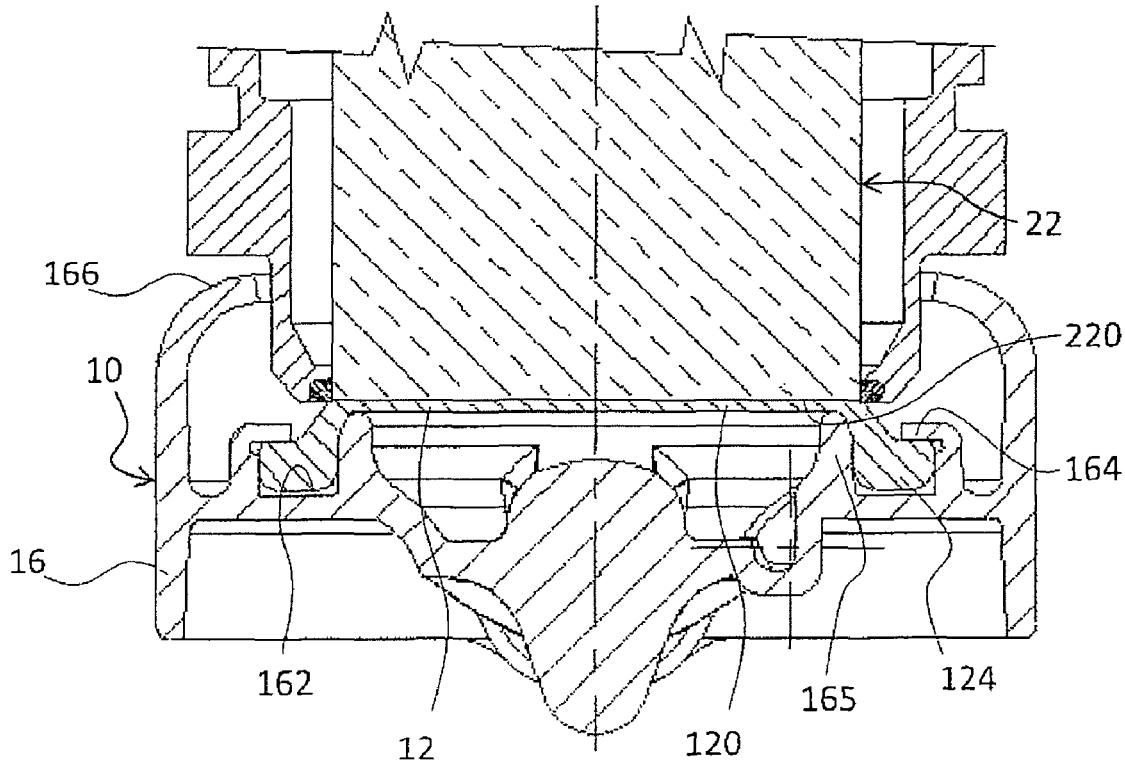

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-2 and 4-6 are cancelled.

Claim 7 is determined to be patentable as amended.

Claims 8-15, dependent on an amended claim, are determined to be patentable.

New claims 16-45 are added and determined to be patentable.

Claim 3 was not reexamined.

7. A pressure dome for cooperating with a pressure sensor, said pressure dome comprising:
  a main body [which defines] *configured to mechanically interface with a pressure sensor housing of a machine, the main body defining* an inlet and an outlet configured to enable hydraulic connection to a pipe, and
  a membrane [according to claim 1] *for the pressure dome* comprising a resilient circular wall configured to close one side of said pressure dome so as to define a partition between an inside of the pressure dome and an outside of the pressure dome; and
  *a circular rim configured to be housed in a main body of the pressure dome,* the resilient circular wall, when there is no difference between pressures acting respectively on an inner surface thereof and on an outer surface thereof, having an outwardly convex form,
  *wherein, when the pressure dome is interfaced with the pressure sensor housing of the machine, the outwardly convex form of the resilient circular wall directly and physically contacts a sensor in the sensor housing.*

16. *A system comprising:*
  *a machine comprising a sensor disposed in a sensor housing;*
  *an extracorporeal circuit configured to be connected to the machine, the extracorporeal circuit comprising:*
    *a pressure dome comprising a main body configured to mechanically interface with the pressure sensor housing of the machine, the pressure dome having an inlet and an outlet*
    *tubing connected to the inlet and the outlet of the pressure dome to allow physiological fluid to flow through the pressure dome; and*
    *a membrane for the pressure dome, the membrane comprising a resilient circular wall configured to close one side of the pressure dome so as to define a partition between an inside of the pressure dome and an outside of the pressure dome; and*
    *a circular rim configured to be housed in the main body of the pressure dome, the resilient circular wall, when there is no difference between pressures acting respectively on an inner surface thereof and on an outer surface thereof, having an outwardly convex form,*
    *wherein, when the pressure dome is mechanically interfaced with the sensor housing of the machine, the outwardly convex form of the resilient circular wall directly and physically contacts the sensor disposed in the sensor housing.*

17. *The system of claim 16 wherein the main body of the pressure dome includes a seat for stably seating the membrane.*

18. *The system of claim 17, wherein the seat includes an edge and an inner wall, and wherein the edge is deformed to fix the membrane inside the seat.*

19. *The system of claim 18, wherein the deformed edge seals an entire circumference of the pressure dome.*

20. *The system of claim 18, wherein the deformed edge is shorter than the inner wall.*

21. *The system of claim 16, wherein the main body includes a second outer edge folded towards an inside of the main body.*

22. *The system of claim 16, further comprising a protective element configured to (i) be combined with the pressure dome in a position intended to receive the pressure sensor and (ii) protect the membrane.*

23. *The system of claim 16, further comprising a rigid ring that fixes the membrane onto the main body of the pressure dome.*

24. *An extracorporeal circuit for a machine, the extracorporeal circuit comprising:*
  *a pressure dome comprising a main body configured to mechanically interface with a pressure sensor housing of the machine, the pressure dome having an inlet and an outlet;*
  *tubing connected to the inlet and the outlet of the pressure dome to allow physiological fluid to flow through the pressure dome;*
  *a membrane for the pressure dome, the membrane comprising:*
    *a resilient circular wall configured to close one side of the pressure dome so as to define a partition between an inside of the pressure dome that is exposed to circulating physiological fluid and an outside of the pressure dome that is isolated from circulating physiological fluid; and*
    *a circular rim configured to be housed in the main body of the pressure dome, wherein the resilient circular wall, when there is no difference between pressures acting respectively on an inner surface thereof and on an outer surface thereof, has an outwardly convex form,*
    *wherein, when the pressure dome is mechanically interfaced with the pressure sensor housing of the machine, the outwardly convex form of the membrane's resilient circular wall directly and physically contacts a flat face of a sensor disposed in the pressure sensor housing.*

25. *The extracorporeal circuit of claim 24 wherein the main body of the pressure dome includes a seat for stably seating the membrane.*

26. *The extracorporeal circuit of claim 25, wherein the seat includes an edge and an inner wall, and wherein the edge is deformed to fix the membrane inside the seat.*

27. *The extracorporeal circuit of claim 26, wherein the deformed edge seals an entire circumference of the pressure dome.*

28. *The extracorporeal circuit of claim 26, wherein the deformed edge is shorter than the inner wall.*

29. The extracorporeal circuit of claim 24, wherein the main body includes a second outer edge folded towards an inside of the main body.

30. The extracorporeal circuit of claim 24, further comprising a protective element configured to (i) be combined with the pressure dome in a position intended to receive the pressure sensor and (ii) protect the membrane.

31. The extracorporeal circuit of claim 24, further comprising a rigid ring that fixes the membrane onto the main body of the pressure dome.

32. A pressure dome for an extracorporeal circuit, the pressure dome comprising:
a main body configured to mechanically interface with a pressure sensor housing of a machine, the main body defining an inlet and an outlet to allow physiological fluid to flow through the pressure dome;
a membrane for the pressure dome, the membrane comprising:
a resilient circular wall configured to close one side of the pressure dome so as to define a partition between an inside of the pressure dome and an outside of the pressure dome; and
a circular rim configured to be housed in the main body of the pressure dome, the resilient circular wall, when there is no difference between pressures acting respectively on an inner surface thereof and on an outer surface thereof, having an outwardly convex form,
wherein, when the pressure dome is mechanically interfaced with the pressure sensor housing of the machine, the outwardly convex form of the resilient circular wall directly and physically contacts a sensor disposed in the pressure sensor housing.

33. The pressure dome of claim 32 wherein the main body of the pressure dome includes a seat for stably seating the membrane.

34. The pressure dome of claim 33, wherein the seat includes an edge and an inner wall, and wherein the edge is deformed to fix the membrane inside the seat.

35. The pressure dome of claim 34, wherein the deformed edge seals an entire circumference of the pressure dome.

36. The pressure dome of claim 34, wherein the deformed edge is shorter than the inner wall.

37. The pressure dome of claim 32, wherein the main body includes a second outer edge folded towards an inside of the main body.

38. The pressure dome of claim 32, further comprising a protective element configured to (i) be combined with the pressure dome in a position intended to receive the pressure sensor and (ii) protect the membrane.

39. The pressure dome of claim 32, further comprising a rigid ring that fixes the membrane onto the main body of the pressure dome.

40. A pressure dome for cooperating with a pressure sensor, the pressure dome comprising:
a main body which defines an inlet and an outlet configured to enable hydraulic connection to a pipe, wherein the main body comprises a seat formed of an outer folded edge and an inner wall, the inner wall having a height that is greater than the outer folded edge; and
a membrane for the pressure dome, the membrane comprising:
a resilient circular wall configured to close one side of said pressure dome so as to define a partition between an inside of the pressure dome and an outside of the pressure dome; and
a circular rim configured to be housed in a main body of the pressure dome, the resilient circular wall, when there is no difference between pressures acting respectively on an inner surface thereof and on an outer surface thereof, having an outwardly convex form
wherein the circular rim is shaped to fit within the seat of the pressure dome such that contact of the circular rim with the inner wall and the outer edge folded over the circular rim forms a bead that prevents passage of liquid between a bottom surface of the membrane and a top surface of the membrane.

41. The pressure dome of claim 40, wherein the seat is configured to stably seat the membrane.

42. The pressure dome of claim 40, wherein the edge enables fixing of the membrane inside the seat by a beading.

43. The pressure dome of claim 42, wherein the beading seals an entirety of the pressure dome.

44. The pressure dome of claim 40, further comprising a protective element configured to (i) be combined with the pressure dome in a position intended to receive the pressure sensor, and (ii) protect the membrane.

45. The pressure dome of claim 40, further comprising a rigid ring that fixes the membrane onto the main body of the pressure dome.

\* \* \* \* \*